United States Patent
Razdan et al.

(10) Patent No.: US 12,128,196 B2
(45) Date of Patent: *Oct. 29, 2024

(54) PROTECTIVE COVER, METHODS OF MAKING AND USING A PROTECTIVE COVER AND KITS HAVING A PROTECTIVE COVER

(71) Applicant: CAREANDWEAR II, INC., New York, NY (US)

(72) Inventors: Chaitenya Razdan, New York, NY (US); Caroline Smith, New York, NY (US); Susan Jones, New York, NY (US)

(73) Assignee: CareandWear II, Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/416,064

(22) Filed: Jan. 18, 2024

(65) Prior Publication Data

US 2024/0149022 A1 May 9, 2024

Related U.S. Application Data

(63) Continuation of application No. 17/703,590, filed on Mar. 24, 2022, now Pat. No. 11,911,577, which is a
(Continued)

(51) Int. Cl.
*A61M 25/02* (2006.01)
*A61F 15/00* (2006.01)
(Continued)

(52) U.S. Cl.
CPC ........... *A61M 25/02* (2013.01); *A61F 15/004* (2013.01); *B32B 5/08* (2013.01); *B32B 7/12* (2013.01);
(Continued)

(58) Field of Classification Search
CPC .............. A61M 25/02; A61M 2209/06; A61M 2205/0216; A61M 2205/0205;
(Continued)

(56) References Cited

U.S. PATENT DOCUMENTS

| 4,470,410 A | 9/1984 | Elliott |
| 5,395,675 A | 3/1995 | Altholz et al. |

(Continued)

OTHER PUBLICATIONS

Extended European Search Report of related European Patent Application No. 15827136.1 dated Dec. 17, 2017.
(Continued)

*Primary Examiner* — Tarla R Patel
(74) *Attorney, Agent, or Firm* — ArentFox Schiff LLP (57) ABSTRACT

A protective cover for an affected area of a patient, particularly associated with an insertion site of a catheter or other puncture or opening in a patient's skin, comprising a body portion including an aperture, and a window portion, wherein the body portion and window portion each optionally comprises an antimicrobial composition. Aspects of the present invention provide articles, systems and kits for covering an incision, wound or catheter insertion site with a protective cover, and methods of using and making the protective cover.

14 Claims, 6 Drawing Sheets

Related U.S. Application Data continuation of application No. 15/421,170, filed on Jan. 31, 2017, now abandoned, which is a continuation of application No. PCT/US2015/043276, filed on Jul. 31, 2015.

(60) Provisional application No. 62/032,367, filed on Aug. 1, 2014.

(51) Int. Cl.
    *B32B 5/08*          (2006.01)
    *B32B 7/12*          (2006.01)
    *B32B 27/12*        (2006.01)
    *B32B 27/34*        (2006.01)

(52) U.S. Cl.
CPC .............. *B32B 27/12* (2013.01); *B32B 27/34* (2013.01); *A61M 2025/0246* (2013.01); *A61M 2025/0273* (2013.01); *A61M 2205/0205* (2013.01); *A61M 2205/0216* (2013.01); *A61M 2209/06* (2013.01); *B32B 2255/02* (2013.01); *B32B 2255/10* (2013.01); *B32B 2260/021* (2013.01); *B32B 2262/062* (2013.01); *B32B 2262/14* (2013.01); *B32B 2270/00* (2013.01); *B32B 2307/7145* (2013.01); *B32B 2307/724* (2013.01); *B32B 2307/7265* (2013.01); *B32B 2535/00* (2013.01)

(58) Field of Classification Search
CPC .. A61M 2205/0273; A61M 2205/0246; A61M 2025/0246; A61M 2025/0273; A61F 15/004; B32B 5/08; B32B 7/08; B32B 2535/00; B32B 7/12; B32B 27/34; B32B 27/12; B32B 2262/14; B32B 2262/062; B32B 2255/02; B32B 2255/10; B32B 2307/724; B32B 2307/7145; B32B 2307/7265; B32B 2270/00; B32B 2260/021

See application file for complete search history.

(56) References Cited

U.S. PATENT DOCUMENTS

| | | |
|---|---|---|
| 5,456,660 A | 10/1995 | Reich et al. |
| 5,897,519 A | 4/1999 | Shesol et al. |
| 6,011,194 A | 1/2000 | Buglino et al. |
| 8,110,538 B2 | 2/2012 | Martin et al. |
| 8,383,205 B2 | 2/2013 | Rosing et al. |
| 9,566,417 B1 | 2/2017 | Propp |
| 10,188,835 B1 | 1/2019 | Mcclarren et al. |
| 11,911,577 B2 * | 2/2024 | Razdan ................ B32B 27/34 |
| 2005/0020977 A1 | 1/2005 | Eldridge et al. |
| 2007/0299407 A1 * | 12/2007 | Dixon ................ A61M 25/02 |
| | | 604/243 |
| 2008/0071224 A1 | 3/2008 | Forsyth |
| 2010/0022928 A1 | 1/2010 | Langen |
| 2010/0257654 A1 * | 10/2010 | Waters ................ A41B 13/06 |
| | | 2/69.5 |
| 2012/0046612 A1 | 2/2012 | Scheremet et al. |
| 2013/0012883 A1 * | 1/2013 | Fitzgerald ............ A61M 39/08 |
| | | 604/179 |
| 2013/0110048 A1 | 5/2013 | Herzog |
| 2013/0204190 A1 | 8/2013 | Wilborn et al. |
| 2013/0251590 A1 | 9/2013 | Golden et al. |
| 2013/0310754 A1 | 11/2013 | Kutsch |
| 2014/0004208 A1 | 1/2014 | Golden et al. |
| 2014/0090651 A1 | 4/2014 | Melendez |
| 2014/0188079 A1 * | 7/2014 | Simons ................ A61M 25/02 |
| | | 604/179 |

OTHER PUBLICATIONS

International Preliminary Report on Patentability issued from the International Preliminary Examining Authority in related International Application No. PCT/US2015/043276, mailed on Sep. 19, 2016.

International Search Report of related International Patent Application No. PCT/US2015/043276 dated Oct. 23, 2015.

Written Opinion of related International Patent Application No. PCT/US2015/043276 dated Oct. 23, 2015.

Communication from the European Patent Office in related European Patent Application No. 15827136.1 dated Aug. 12, 2019.

Communication from the European Patent Office in related European Patent Application No. 15827136.1 dated Feb. 3, 2020.

* cited by examiner

PROTECTIVE COVER, METHODS OF MAKING AND USING A PROTECTIVE COVER AND KITS HAVING A PROTECTIVE COVER

CROSS REFERENCE TO RELATED APPLICATIONS

This application is a Continuation application of U.S. patent application Ser. No. 17/703,590, entitled "PROTECTIVE COVER, METHODS OF MAKING AND USING A PROTECTIVE COVER AND KITS HAVING A PROTECTIVE COVER", filed on Mar. 24, 2022, which is a Continuation application of U.S. patent application Ser. No. 15/421,170, entitled "PROTECTIVE COVER, METHODS OF MAKING AND USING A PROTECTIVE COVER AND KITS HAVING A PROTECTIVE COVER", filed on Jan. 31, 2017, which claims benefit under 35 U.S.C. 120 to International Patent Application No. PCT/US2015/043276, filed Jul. 31, 2015, which claims benefit under 35 U.S.C. 119(e) to U.S. Provisional Patent Application No. 62/032,367, filed Aug. 1, 2014, the entirety of each of which are incorporated by reference herein.

FIELD OF THE INVENTION

Aspects of the present invention relate to a protective cover for an affected area of a patient, particularly associated with an insertion site of a catheter or other puncture or opening in a patient's skin. Aspects of the present invention provide articles, systems and kits for covering an incision, wound or catheter insertion site with a protective cover and methods of using and making the protective cover.

BACKGROUND OF THE INVENTION

A patient's skin may be incised, punctured, cut or otherwise opened for numerous reasons. For example, catheters are routinely used by physicians to access a patient's vascular system to introduce fluids, nutritional substances and medicines. A peripherally inserted central catheter ("PICC"), for example, is typically inserted into a patient's peripheral vein, such as in the patient's upper arm. The PICC tube is advanced in the vein until its tip terminates in a large vein near the patient's heart to gain intravenous ("IV") access. While a PICC is similar to a standard IV, it is less invasive and often remains in the patient for much longer periods than other venous access devices.

Although relatively less invasive, PICCs, like other devices, leave a tube, access valve (sometimes two or three tubes and valves) and/or other hardware on the outer surface of the patient's skin, that typically remains stitched and/or taped in place. Therefore, a PICC may feel cumbersome to the patient and be difficult to cover up and protect from knocking, catching, pulling and displacement. Moreover, the insertion site may leak, turn black and yellow or may otherwise appear unsightly, which is a constant reminder of the treatment to the patient and could cause the patient to feel uncomfortable. In addition, patients normally cannot wash the area, and yet the insertion site must remain clean to avoid infection from bacteria and other microorganisms. Approximately 8 to 25% of PICC lines become infected and can lead to mortality. In addition, the dressing protecting the PICC site often requires air to activate the chemicals embedded in the dressing that fight infection. This can be seen, for example, in the 3M™ Tegaderm™ dressing.

Whether for purposes of protecting a PICC or other catheter insertion site or a wound or surgical incision, there is a need for a protective cover that provides the area with protection while also allowing air to access the area, which may allow breathability to the area and help prevent infection. There is also a need for a protective cover having antimicrobial properties.

BRIEF SUMMARY OF THE INVENTION

Aspects of the invention are directed to a protective cover for an affected area of a subject, comprising: a body portion comprising an aperture, and a window portion comprising a material that allows air to access the area. According to some aspects of the invention, the body portion and/or the window portion may comprise a treatment composition, such as an antimicrobial and/or disinfectant and/or decontaminant. According to some aspects, the body portion and/or the window portion may comprise a fabric meeting the requirements for comprising the treatment composition. For example, according to some aspects, the body portion may comprise a minimum of about 25% cotton and an elastic material (for example, lycra and/or spandex) for security of a PICC line and also comfort for the wearer. Aspects of the invention also relate to a method of forming a protective cover for a catheter insertion site, the method comprising: providing a body portion, the body portion having an approximately trapezoidal outer shape prior to being worn or fully assembled, with at least two side edges and two end body edges, and an aperture positioned generally central between the two end body edges, attaching a window portion to the body portion so as to cover at least a portion of the aperture, attaching at least two side edges of the body portion to one another at least at or near each of the two end body edges, so as to form at last a partial tubular shape.

Aspects of the invention are also directed to a kit for covering a catheter insertion site, comprising: a body portion comprising an aperture, a window portion comprising a material that allows air to access the area, and other features for protectively surrounding the protective cover. These other portions may comprise any material suitable for surrounding the protective cover, for example, a poly bag and/or cardboard around the protective cover. According to some aspects of the invention, the body portion and/or the window portion may comprise a treatment composition, such as an antimicrobial and/or disinfectant and/or decontaminant. According to some aspects, the body portion and/or the window portion may comprise a fabric meeting the requirements for incorporating the treatment composition. For example, according to some aspects, the body portion may comprise a minimum of about 25% cotton and an elastic material (for example, lycra and/or spandex) for security and comfort of a PICC line; in other variations the body portion may be much less than 25%. Aspects of the invention also relate to a method of using a kit for covering an affected area of a subject, the kit comprising a body portion comprising an aperture, a window portion comprising a material that allows air to access the area, and packaging for protectively surrounding the protective cover, the method comprising: providing the protective cover to a subject having an affected area of a body part; and covering the affected area with the protective covering. According to some aspects of the invention, the body portion and/or the window portion may comprise a treatment composition, such as an antimicrobial and/or disinfectant and/or decontaminant. According to some aspects, the body portion and/or the window portion may comprise a fabric meeting the requirements for incorporating the treatment composition. For example, according to some aspects, the body portion may comprise a minimum of about 25% cotton and an elastic material (for example, lycra and/or spandex) for security and comfort of the PICC line; in other variations the body portion may be much less than 25% and may involve other materials.

Additional advantages and novel features in accordance with aspects of the invention will be set forth in part in the description that follows, and in part will become more apparent to those skilled in the art upon examination of the following or upon learning by practice thereof.

DETAILED DESCRIPTION

These and other features and advantages in accordance with aspects of this invention are described in, or are apparent from, the following detailed description of various example aspects.

Aspects of the present invention are directed to an article for covering an affected area of a patient, such as an insertion site of a catheter (e.g., a PICC). Aspects of the present invention are also directed to methods and kits for making and using a protective cover for covering an affected area of a patient, such as for covering an insertion site of a catheter.

Aspects of the present invention are described with respect to FIGS. 1-4. These figures illustrate example variations of components that may be incorporated in many different designs of the protective cover, as well as in methods and kits for making and using the same.

It is understood that FIGS. 1-4 are not meant to be an exhaustive description of the designs and configurations for the protective cover or methods and kits for making and using the same. Rather, these figures show some example components and illustrate some example concepts that may be used to construct any number of protective coverings and kits.

Figure 1A:
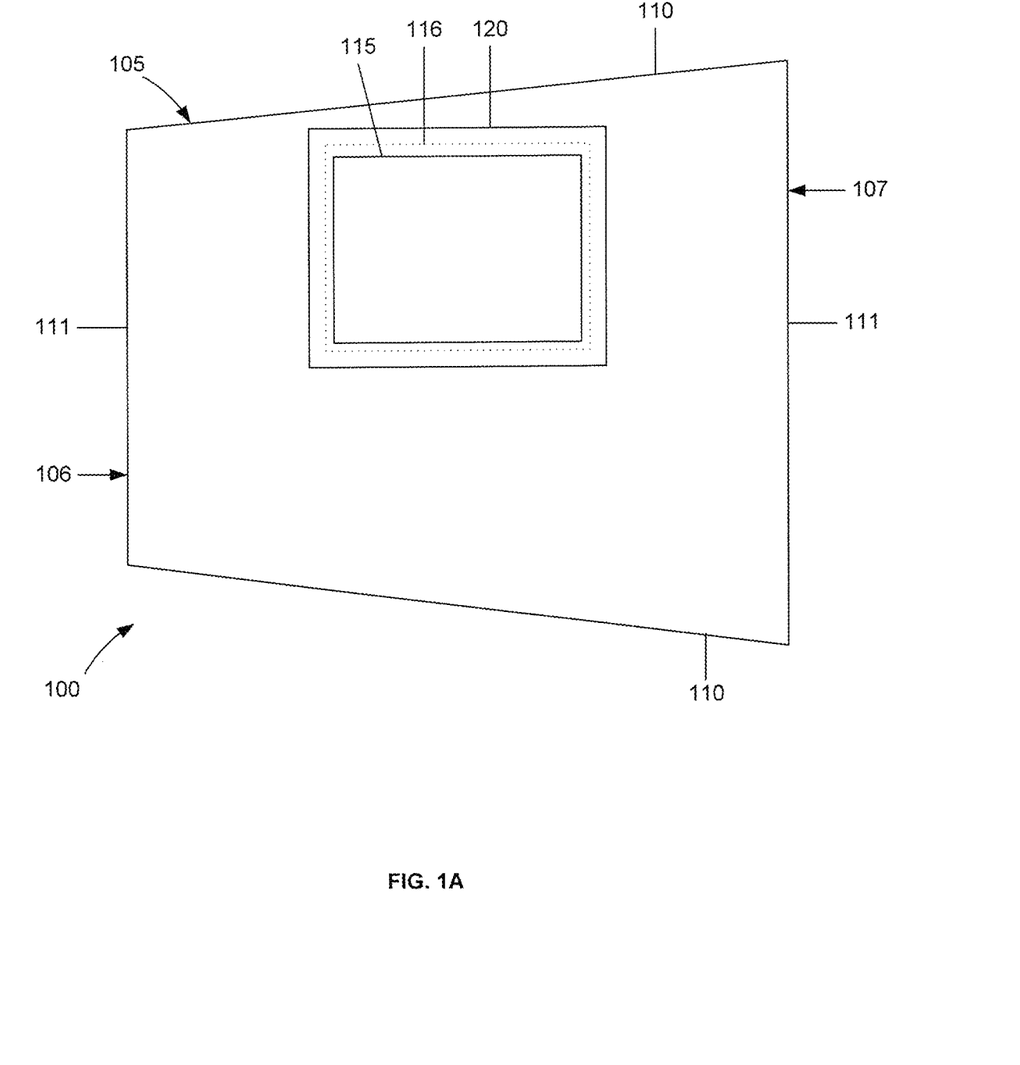
FIG. 1A illustrates aspects of a protective cover according to aspects of the invention.

FIG. 1A is a representative view of an example article according to aspects of the present invention. The example article may be a protective cover 100 for covering, for example, an affected area of a patient's skin, such as an insertion site of a catheter (not shown). The catheter may be a PICC or other standard catheter or skin penetration device having external components that may need protection from knocking, catching and pulling, and from bacteria and other microorganisms. The protective cover 100 may include a body portion 105 that forms the main structure for the protective cover 100. The side edges 110 of the body portion 105 may, in relation to the end body edges 111 of the body portion 105, be arranged so that the body portion 105 has a generally trapezoidal shape when in a flat, unassembled position, as shown. Therefore, when the side edges 110 are attached together in a tubular configuration, as will be explained in more detail with reference to FIGS. 2 and 3, the inner diameter of end 106 would be smaller than the inner diameter of end 107. In other aspects, the body portion 105 may be approximately rectangular in shape in a flat position.

In one example aspect, the body portion 105 includes an aperture 115 in which a window portion 120 is attached to the body portion 105, for example, via stitching 116 with thread on all sides (or similarly attaching, such as by use of an adhesive, zipper, buttons, snaps or other suitable attachment mechanism and/or method).

Figure 1B:
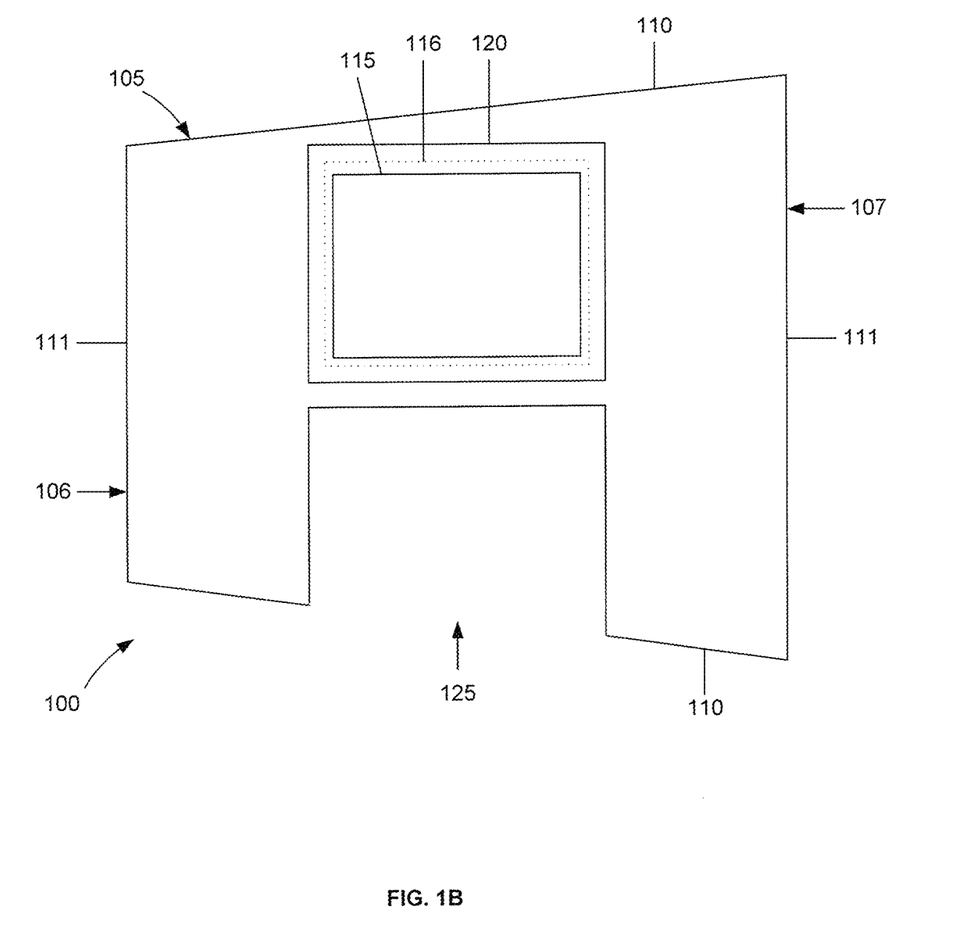
FIG. 1B illustrates aspects of a protective cover according to aspects of the invention.

In another example aspect, as shown in FIG. 1B, the body portion 105 may also include a notch or other similar feature 125 in order to reduce the amount of material required to make the body portion 105 and to aid in comfort for the patient (e.g., by reducing pressure that may be applied to the affected area as covered by the window portion 120, when the protective cover 100 is worn). For example, when the side edges 110 are attached to form a tubular configuration of the protective cover, as will be explained in more detail with reference to FIG. 2, one side of the tubular protective cover will have the window portion, whereas the opposite side, corresponding to the notch 125, will not have any material (i.e., there is a space in the body portion). In some variations, the body portion 105 may not include the notch 125 so that the material is continuous along the entire length of each of the side edges 110 of the protective cover 100, as shown in FIG. 1A. In other variations, the body portion 105 may include a pocket (not shown) stitched thereto for receiving and storing tubes or other hardware associated with, for example, a catheter.

In an example configuration, the entire length of the protective cover 100, for example, the distance between the end body edges 111, may be about 4 to about 10 inches. The width of the body portion 105, for example, the length of each of the end body edges 111, may be about 4 to about 10 inches. In the case of a trapezoidal configuration of the body portion 105, the ratio of the length of the longer end body edge 111 to the length of the shorter end body edge 111 may be about 2.5 to about 8 inches (a ratio of 0.83 to about 0.94). According to some aspects, the entire length of the protective cover, the width of the body portion 105, and/or the ratio of the length of the longer end body edge 111 to the length of the shorter end body edge 111 may be varied in order to fit comfortably on patients of various sizes. For example, these dimensions may be increased and/or decreased to provide necessary protection to the affected area while also decreasing unnecessary constraint.

In one aspect, the shape of the aperture 115 may be approximately rectangular. For example, the sides of the aperture 115 may be about 2.5 to 4.0 inch. In one example aspect, the lateral sides of the aperture 115 may be about 2.5 to 4.0 inch, and the longitudinal sides of the aperture 115 may be about 2.25 to 3.5 inch. The windows may range from about 1.5 to 3 inches to 4 to 4.5 inches at max. In another example aspect, the aperture may be circular with a diameter of about 2.25 to about 4.0 inch. According to some aspects, the size and shape of the aperture 115 may be varied in order to increase comfort and usability, and to ensure that the protective cover is to scale for a wide range of customers. For example, the length of the aperture 115 may be increased by about 2 inches so that a window portion 120 therein would comprise more of the protective cover lengthwise. In another example, the width of the aperture 115 may be decreased by about half an inch.

The body portion 105 may comprise a soft, lightweight, flexible, stretchy material or fabric. According to some aspects, the body portion 105 may comprise a fabric that meets the requirements for incorporating a certain treatment composition, such as an antimicrobial and/or disinfectant and/or decontaminant. For example, according to some aspects, the body portion may comprise a minimum of about 25% cotton or equivalent material, such as beachwood and modal, and combinations thereof. The body portion 105 may include spandex or other elastic materials including nylon and other polymers (e.g., Lycra® by E. I. Du Pont de Nemours and Company of Delaware) or combinations thereof. For example, the body portion 105 may include up to 89% by weight of spandex or similar materials or combinations thereof.

Figure 5:
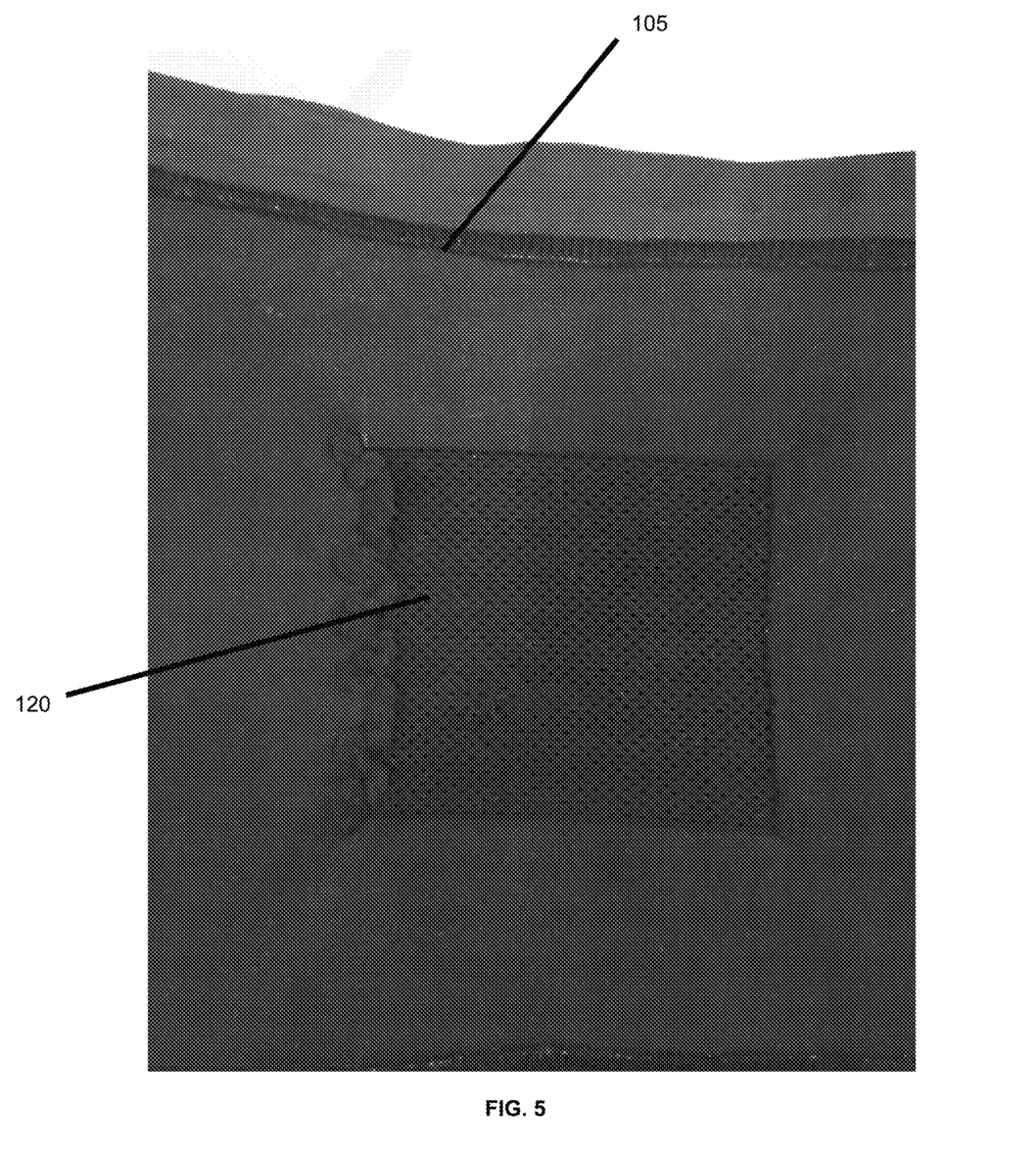
FIG. 5 is a photostat showing aspects of a protective cover having a window portion incorporated therein according to aspects of the invention.

In certain aspects, the aperture 115 may create a space in which the window portion 120 is inserted by coupling (e.g. stitching) the edges of the material or fabric of the window portion 120 to the body portion 105, for example, around the periphery of the aperture 115. According to some aspects, the hem of the edges of the window portion material outside the seam (e.g., outside the stitching) may be removed after the window portion 120 is coupled to the body portion 105. According to some aspects, the amount of window portion material remaining outside the seam may be minimized to the lowest value that the protective cover will tolerate (e.g., before the window portion 120 cannot be securely coupled to the body portion 105). Alternatively, according to some aspects, the window portion may be incorporated into the body portion. For example, according to some aspects, the window portion may not be or may not comprise a separate component inserted into an aperture in the body portion, but may instead be formed into or with the body portion. For example, as shown in FIG. 5, the window portion 120 may be incorporated into the body portion 105, for example, by knitting or weaving the window portion 120 as part of knitting or weaving the body portion 105.

The window portion 120 may also comprise a soft, lightweight, flexible, stretchy material that meets the requirements for incorporating a certain treatment composition, such as an antimicrobial and/or disinfectant and/or decontaminant. For example, according to some aspects, the body portion may comprise a minimum of 25% cotton or equivalent material, such as beachwood and modal, and combinations thereof. The composition of the window portion 120 material may be different than that of the material for the body portion 105. For example, the window portion 120 may be lighter than the material of the body portion 105 and in some aspects, may comprise a mesh material. As used herein, the term "mesh" indicates any material which allows air to pass therethrough, for example, by comprising pores. For example, the window portion 120, may be porous having pores of about 0.05 mm to 4.0 mm. In certain aspects, the pores may be approximately uniform in shape and size. The window portion 120, in certain aspects, may be breathable to permit oxygen (e.g., from air) to flow through the window portion 120 to the affected area of the patient, for example, the insertion site of the catheter. In certain aspects, the window portion 120 may be stretchy and soft as to avoid pressing of the PICC line into a patient's arm, which may be uncomfortable. The window portion 120 may contain up to 100% by weight of spandex or other elastic materials including nylon and other polymers (e.g., Lycra®) or combinations thereof.

According to some aspects, the material comprised by any of the protective cover's components may not significantly absorb sweat, such that the protective cover does not provide an odor even after a patient wearing it has sweat, for example, after exercise.

According to some aspects, the protective cover's components may include material used to couple portions of the protective cover. The composition of the material may be such that all of the protective cover's seams are not disturbed by certain use thereof. For example, the composition of the material may be such that all seams remain intact after washing the protective cover in an industrial washing machine and dryer (150° C.).

The protective cover may comprise care instructions specific for the materials comprised therein. For example, the protective cover may have a label indicating proper washing conditions (e.g., "machine wash cold, lay flat to dry" or "machine wash warm, dry cycle low" or "cold or warm water with or without bleach and low dry cycle or air dry").

According to some aspects, the material, including any portion of the protective covering, may be of a suitable composition to allow printing thereon, for example, to allow designs on the protective covering.

Figure 2:
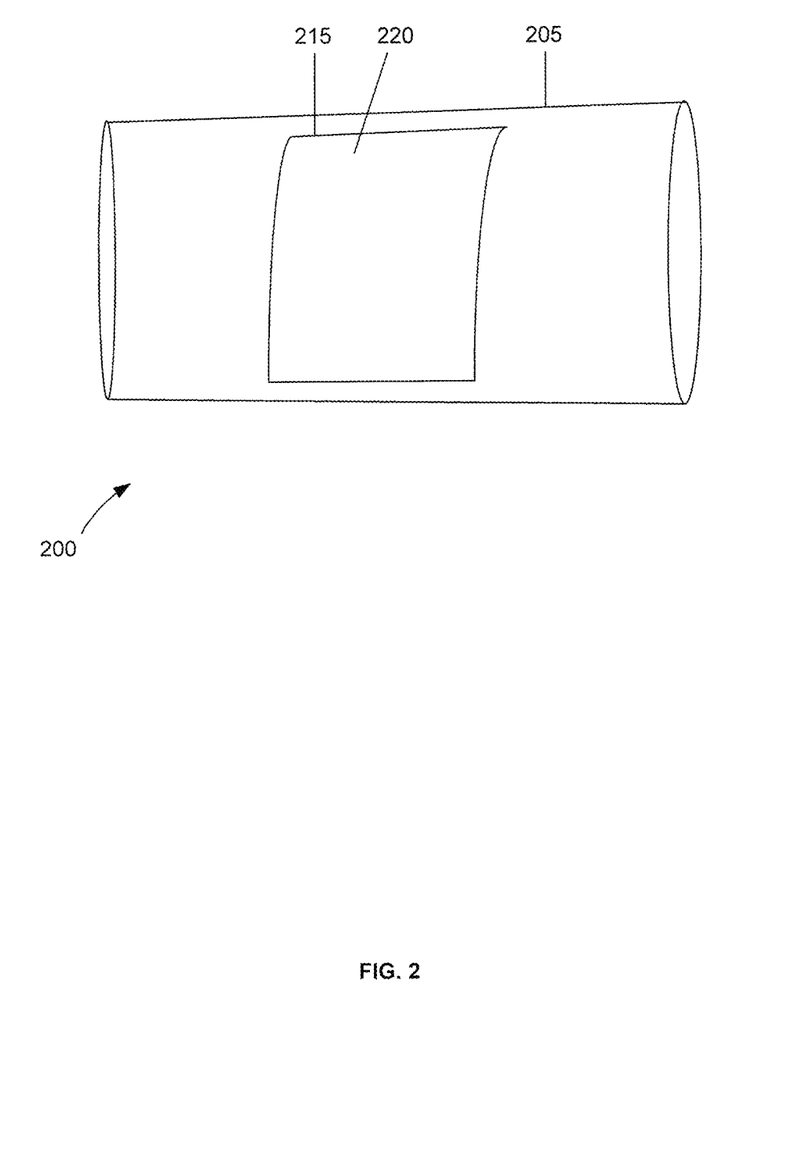
FIG. 2 illustrates aspects of a protective cover according to aspects of the invention.

FIG. 2 is a representative view of a protective cover 200 in an assembled and/or worn arrangement, according to aspects of the invention. To form the protective cover 200 shown in FIG. 2, the side edges 110 depicted in FIG. 1 may be attached to one another so as to form generally tubular portions near the end body edges 111 of the protective cover 200. For example, the side edges 110 may be stitched to one another with a fabric that meets the requirements for incorporating a certain treatment composition, such as an antimicrobial and/or disinfectant and/or decontaminant. For example, the side edges may be stitched to one another with cotton thread or equivalent material having at least about 25% by weight of the cotton or equivalent material. Although not shown, the side edges 110 may similarly be attached by Velcro® made by Velcro S. A. Corporation of Switzerland (or similar material), zippers, buttons, snaps or other fastening device(s). Thus, any suitable features or methods for fastening the side edges 110 of the protective covering 200 may be used, and may also, for example, be durable and antimicrobial. The inner diameter of the protective cover 200 in the tubular configuration may be sized to fit over a limb of a particular subject. In certain example aspects, the inner diameter at one end of the protective cover 200 may be larger than the inner diameter at the opposite end. For example, the inner diameter may decrease from one end to another of the protective cover 200. In one example aspect, the inner diameter at the large end may be sized to fit an upper portion of a limb whereas the inner diameter at the smaller end is sized to fit a lower portion of a limb.

The protective covering 200 shown in FIG. 2, may include a body portion 205 and an aperture 215, similarly to as described in connection with FIG. 1. The protective covering 200 may also include a window portion 220, similarly to as described in connection with FIG. 1. In use, a patient, alone or with assistance from a healthcare provider, may insert a hand, foot or other limb into the tubular protective cover 200 and then slide the protective cover 200 up the limb to cover an affected area, for example, the insertion site of a catheter and associated hardware. It should be noted that the protective cover 200 may also be used to cover surgical incisions, stitches, scars or other wounds or openings in a patient's skin. The window portion 220 may be positioned over the affected area, for example, the insertion site of a catheter, to ensure sufficient air is permitted to flow through the protective cover 200 to the area. The window portion may be positioned over the affected area directly, or it may be positioned over a separate covering (e.g., a dressing, a bandage and/or tape).

In its tubular configuration, the protective cover 200 may provide slight to moderate compression to the patient's limb and any associated hardware to ensure the protective cover 200 keeps any hardware in place and does not substantially move during use. In certain aspects, the compression should not be significant enough to cause pain or discomfort to the affected area, for example, to the insertion site and associated hardware of a catheter. For example, the protective cover 200 may provide a compression force without restricting blood flow or causing discomfort to the patient. The protective cover 200 may also elastically stretch so that the inner diameter and/or circumference of the protective cover 200 is selected to be slightly smaller (i.e., to provide compression) than the inner diameter and/or circumference of the limb to be worn upon, the material being stretchable so as to be comfortably, but securely (and/or compressibly), worn. In other aspects, the protective cover 200 should also readily stretch over the affected area and any associated hardware for fast and easy application or removal. Therefore, the inner diameter of the protective cover 200 before being worn (i.e., the "ready to wear" or "unstretched" diameter) may be smaller than the inner diameter of the article once it is on a subject's limb. For example, the inner diameter may expand from an unstretched ("ready to wear") position to a stretched ("worn") position. Furthermore, several protective covers 200 may be formed in a range of sizes selectable as appropriate for the size of the limb and the level of desired comfort or compression versus securing tightness for the wearer.

In one aspect, the protective cover 100, 200, for example, the body portion 105 and the window portion 120, either alone or after assembly, may be treated, impregnated and/or coated with an antimicrobial and/or disinfectant and/or decontaminant composition. The treatment composition may include, for example, Sanogiene™ made by BioMed Protect, LLC of St. Louis, MO 63132, which demonstrably reduces various bacterium and colony counts of MRSA, Staph. Aureus, *E. Coli*, Kleb. Pneumoniae, VRE, Enterococcus, Acinetobacter and *C. difficile* with effective kill rates of 99.99% or better at 24 hours and up to 98% within 8 hours, independent of size of the contaminant and colony count. The treatment composition may be formulated to effectively kill and largely eliminate all bacteria that contact the surfaces of the protective cover 100, 200; in some variations such treatment composition may be included in some portions of the cover, but not, for example, the aperture 115 or window portion 220. For example, the protective cover 100, 200 treated with the treatment composition may be formulated to kill microbial pathogens that threaten health and safety and other environmental bacteria or microorganisms that may cause infection or irritation. The treatment composition may also be formulated to be non-toxic and safe to use for materials that contact skin In aspects, the materials of the protective cover 100, 200 may be treated with an antimicrobial and/or decontaminant composition, including an aqueous solution of peroxides and peracids having equilibrium reaction products, a photo reactive surfactant, and a polymer, the polyer interacting with the peroxides and peracids as described and claimed, for example, in U.S. Pat. No. 8,110,538 to BioMed Protect, LLC, which is hereby incorporated herein by reference it is entirety. In certain aspects, the treatment composition includes an aqueous solution of peroxides and peracids having equilibrium reaction products, an anionic photoreactive surfactant containing a phosphate ester with a hydrophilic polyoxyethylene chain having a range of PEO-3 to PEO-9 and an R-terminal group of a lipophilic alkyl chain from C9 to C13 or a nonylphenol. The treatment composition may further contain a non-ionic polymer containing lactam which is polyvinyl pyrrolidone in an amount from about 0.015% to about 6% by weight such that the non-ionic polymer containing lactam interacts with the peroxides and peracids to form complexes and forms associations and adducts with the anionic photoreactive surfactant containing phosphate ester. These associations and adducts may provide additional reactive chemistry which enhances the microbicidal efficacy of the treatment composition.

In other aspects, the material of the protective cover 100, 200 may be treated with disinfectant compositions, such as are disclosed in U.S. Publication No. 2014/0004208 to BioMed Protect, LLC, which is hereby incorporated herein by reference it is entirety. In certain aspects, the disinfectant composition may include a peroxide, a peracid, an anionic surfactant, a nonionic polymer, a linear fatty alcohol and an alkyl pyrrolidone.

In one aspect, the material of the protective cover 100, 200 may be treated with an antimicrobial composition in accordance with methods described, for example, in U.S. Pat. No. 8,383,205 to BioMed Protect, LLC, which is hereby incorporated herein by reference it is entirety. In certain aspects, the method may include applying an aqueous solution of an antimicrobial composition including water, an organic acid, chitosan and one or more heterocyclic N-halamine compounds, where the organic acid is present at a concentration of about 0.2% to 1.0% by weight of solution, to the protective cover 100, 200, and heating the protective cover 100, 200 (e.g., in a drying machine) to cure the antimicrobial composition. The pH of the treatment composition may be balanced during treatment of the protective cover 100, 200 to maintain efficacy.

In other aspects, the protective cover 100, 200 may be treated with an antimicrobial composition in accordance with methods described in U.S. Publication No. 2013/0251590 to BioMed Protect, LLC, which is hereby incorporated herein by reference it is entirety. In aspects, the protective cover 100, 200 may be treated with a microbicidal composition by applying the microbicidal composition to the protective cover 100, 200 to form a thin layer that wets the material, the microbicidal composition including hydrogen peroxide at a concentration of about 0.4 to 8% by weight, peracetic acid at a concentration of about 0.02 to 0.55% by weight, acetic acid at a concentration of less than about 8% by weight, phosphate ester surfactant at a concentration of about 0.01 to 0.5% by weight, water soluble polymer containing lactam at a concentration of about 0.01 to 0.5% by weight, less than 0.2% by weight of stabilizers including inorganic phosphates, phosphonates, organic phosphonic acids or their salts, or ethylenediaminetetracetic acid or its sodium salt, less than 1 ppm of mono- and divalent metal ions, less than about 1 ppm of halide ions and a balance of water. The protective cover 100, 200 may also be contacted with the microbicidal composition for greater than about 25% but less than or equal to about 100% of the evaporation time of the thin layer.

In certain aspects, the protective cover 100, 200 may be part of a kit for covering an affected area of a patient, for example, an insertion site of a catheter and associated hardware. The kit may include instructions for using, washing and drying the protective cover 100, 200. The kit may also include polycarbonate and/or cardboard packaging for the protective cover 100, 200 to ensure cleanliness prior to use. The kit may also include a washing bag for washing the protective cover 100, 200, for example, by placing the protective cover inside the bag before washing. The kit may include bleach and/or detergent and/or a bleach formula and/or bleach-detergent formula for washing the protective cover 100, 200. The protective cover 100, 200 may also be part of a PICC kit. The kit for inserting a catheter may include one or more of the following: a needle, a syringe, a catheter tube, a one-way valve for the catheter, a Y connector, an external tube, a lumen, the protective cover 100, 200, antiseptic wipes, gauze, a dressing for covering the insertion site, medical tape, instructions for installing the catheter, and instructions for using, washing and drying the protective cover 100, 200.

Figure 3:
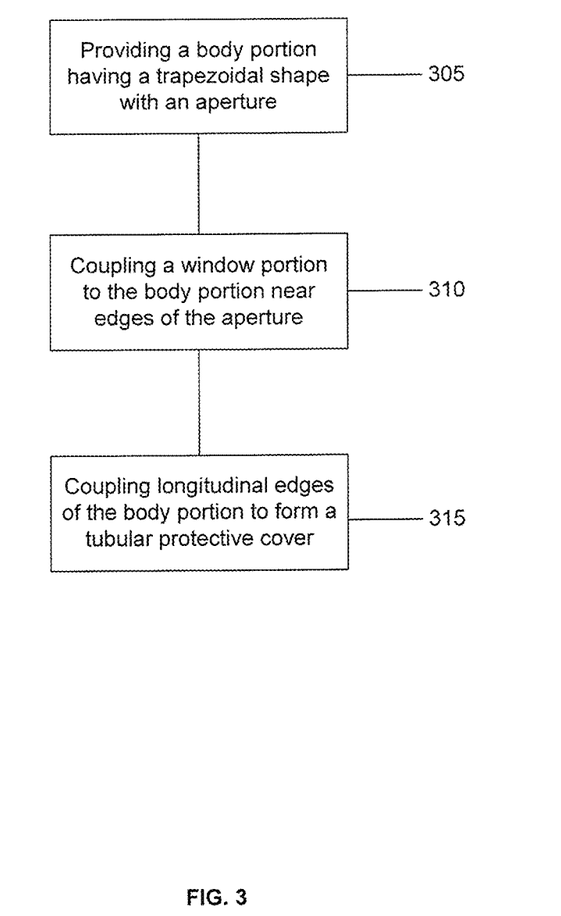
FIG. 3 provides a flow chart of a method for forming a protective cover according to aspects of the invention.

FIG. 3 provides a flowchart of a representative method 300 of forming a protective cover in accordance with aspects of the invention. At 305, the method 300 may include providing a body portion having an approximately trapezoidal shape with an aperture positioned within the body portion. At 310, the method 300 may include attaching a window portion to the body portion near edges of the aperture. At 315, the method 300 may include attaching side (e.g., longitudinal) edges of the body portion to form a tubular protective cover.

Figure 4:
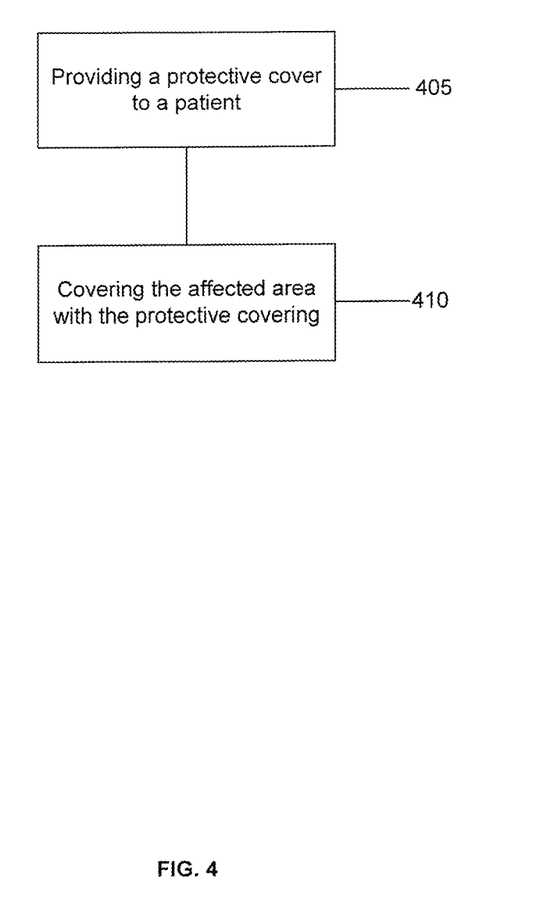
FIG. 4 provides a flow chart of a method of using a kit for covering a catheter insertion site according to aspects of the invention.

FIG. 4 provides a flowchart of a representative method 400 of using a kit according to aspects of the invention. The kit may include components and devices as discussed above. According to the method 400, at 405 the method may include providing a protective cover to a patient having an affected area of a body part. At 410, the method may include covering the affected area with the protective covering.

While aspects of this invention have been described in conjunction with the example features outlined above, alternatives, modifications, variations, improvements, and/or substantial equivalents, whether known or that are or may be presently unforeseen, may become apparent to those having ordinary skill in the art. Accordingly, the example aspects of the invention, as set forth above, are intended to be illustrative, not limiting. Various changes may be made without departing from the spirit thereof. Therefore, aspects of the invention are intended to embrace all known or later-developed alternatives, modifications, variations, improvements, and/or substantial equivalents.

What is claimed is:

1. A protective cover for an affected area of a subject, comprising:
   a body portion comprising an aperture and a notch, the body portion comprising a cotton or equivalent material; and
   a window portion,
   wherein the notch and the window portion overlap when the protective cover is worn to cover the affected area of the subject,
   wherein the body portion and window portion each optionally comprises an antimicrobial composition,
   wherein the body portion is formed from a material having an approximately trapezoidal shape prior to assembly or application to the subject, and
   wherein the material having the approximately trapezoidal shape comprises: a first end body edge approximately parallel to a second end body edge, wherein the first end body edge has a first length, and the second end body edge has a second length that is different from the first length.

2. The protective cover of claim 1, wherein the body portion has at least a partial tubular configuration when worn by the subject, wherein an inner diameter of the tubular configuration of the protective cover is 1 to 8 inches.

3. The protective cover of claim 1, wherein the body portion has a length when worn of 4 to 10 inches, and the dimensions of the aperture are 2.5 to 4.0 inches by 2.25 to 3.5 inches.

4. The protective cover of claim 1, wherein the aperture has either an approximately circular shape with a diameter of 2.25 to 3.5 inches, or a rectangular shape having at least two sides of 2 to 4.0 inches.

5. The protective cover of claim 1, wherein the protective cover is machine-washable and dryable.

6. The protective cover of claim 1, wherein the window portion comprises a breathable porous mesh material.

7. The protective cover of claim 6, wherein the breathable porous mesh material has pores from 0.05 mm to 4.0 mm in diameter.

8. The protective cover of claim 1, wherein the protective cover has at least a portion of an approximately tubular shape when positioned over an affected area on an arm or a leg of the subject.

9. The protective cover of claim 1, wherein the affected area is an insertion site of a catheter, such as a peripherally inserted central catheter (PICC).

10. The protective cover of claim 1, wherein the body portion comprises an elastic material and minimum of 25% cotton.

11. A method of forming a protective cover for a catheter insertion site, the method comprising:
    providing a body portion, the body portion having an approximately trapezoidal outer shape prior to being worn or fully assembled, with at least two side edges, a first end body edge, a second end body edge, a notch, and an aperture positioned generally centrally between the two end body edges, wherein:
    the first end body edge is approximately parallel to the second end body edge,
    the first end body edge has a first length, and
    the second end body edge has a second length that is different from the first length, attaching a window portion to the body portion so as to cover at least a portion of the aperture, wherein the notch and the window portion overlap when the protective cover is worn to cover the catheter insertion site,
    attaching the at least two side edges of the body portion to one another at least at or near each of the two end body edges, so as to form at least a partial tubular shape.

12. A kit for covering a catheter insertion site, the kit comprising:
    a protective cover, including:
    a body portion, the body portion having a notch and, an approximately trapezoidal outer shape prior to being worn or fully assembled, wherein the body portion comprises a first end body edge approximately parallel to a second end body edge, and wherein the first end body edge has a first length, and the second end body edge has a second length that is different from the first length; and
    a window portion, wherein the notch and the window portion overlap when the protective cover is worn to cover the catheter insertion site,
    wherein the body portion and the window portion are optionally treated with an antimicrobial composition, and
    packaging for protectively surrounding the protective cover.

13. The kit according to claim 12, wherein the body portion comprises an elastic material and minimum of 25% cotton.

14. The kit of claim 12, wherein the packaging comprises a material selected from a group consisting of polycarbonate and cardboard.

\* \* \* \* \*